US008697134B2

(12) United States Patent
Balasubramanian et al.

(10) Patent No.: US 8,697,134 B2
(45) Date of Patent: Apr. 15, 2014

(54) FACILE ROUTE TO THE SYNTHESIS OF RESORCINARENE NANOCAPSULES

(75) Inventors: Ramjee Balasubramanian, Norfolk, VA (US); Zaharoula M. Kalaitzis, San Diego, CA (US); Srujana Prayakarao, Norfolk, VA (US)

(73) Assignee: Old Dominion University Research Foundation, Norfolk, VA (US)

( * ) Notice: Subject to any disclaimer, the term of this patent is extended or adjusted under 35 U.S.C. 154(b) by 72 days.

(21) Appl. No.: 13/165,103

(22) Filed: Jun. 21, 2011

(65) Prior Publication Data

US 2011/0311639 A1 Dec. 22, 2011

Related U.S. Application Data

(60) Provisional application No. 61/356,707, filed on Jun. 21, 2010.

(51) Int. Cl.

| A61K 9/51 | (2006.01) |
|---|---|
| C08F 136/22 | (2006.01) |
| C08F 8/02 | (2006.01) |
| C08F 8/14 | (2006.01) |
| C08F 2/46 | (2006.01) |
| C08F 8/34 | (2006.01) |

(52) U.S. Cl.
USPC ........ 424/497; 522/169; 526/268; 525/327.2; 525/298; 525/301; 525/303; 525/302; 977/773; 977/788; 977/906

(58) Field of Classification Search
USPC ............... 424/497; 525/327.2, 298, 303, 302, 525/301; 977/906, 773, 788; 522/169
See application file for complete search history.

(56) References Cited

U.S. PATENT DOCUMENTS

| 2004/0229039 A1 | 11/2004 | Wei et al. |
|---|---|---|
| 2005/0240051 A1 | 10/2005 | Yasuda et al. |
| 2006/0083748 A1 | 4/2006 | Wolf et al. |

OTHER PUBLICATIONS

Balasubramanian et al. (Encapsulation and functionalization of nanoparticles in crosslinked resorcinarene shells, J. Mater. Chem. (2007) 17:105-112), 8 pages.*
Balasubramanian et al., Solvent dependent morphologies in thiol-ene photopolymerization: A facile route to the synthesis of resorcinarene nanocapsules, J. Mater. Chem. (2010), 20: 6539-6543 (5 pages).*
Documentation of the August publication date of Balasubramanian ([Retrieved from <URL: https://pubs.rsc.org/en/journals/jounalissues/jm> ], [Downloaded Sep. 24, 2013]0 (2 pages).*
Wei et al., Resorcinarene-Encapsulated Nanoparticles: Building Blocks for Self-Assembled Nanostructures, Journal of Inclusion Phenomena and Macrocyclic Chemistry (2001), 41: 83-86 (4 pages).*

(Continued)

*Primary Examiner* — Jason Sims
*Assistant Examiner* — Miriam A Levin
(74) *Attorney, Agent, or Firm* — Gardner, Groff, Greenwald & Villanueva, P.C.

(57) ABSTRACT

Described is a direct method for the fabrication of resorcinarene nanocapsules by photopolymerization of compounds of formula (I), such as resorcinarene tetraalkene tetrathiol (RTATT), in the absence of any template or preorganization. Further, by varying the polymerization media, a variety of other polymeric architectures like lattices, fibrous networks, and nanoparticles were obtained. The morphology and structure were characterized by transmission electron microscopy, energy dispersive spectroscopy, scanning electron microscopy, dynamic light scattering, infrared and nuclear magnetic resonance spectroscopy. These morphologically distinct resorcinarene polymeric architectures contain residual thiol and ene functional groups offering potential functionalization opportunities.

10 Claims, 10 Drawing Sheets

Microscopic analysis of RTATT polymers prepared by UV irradiation for 3 h in various solvents.

(56) References Cited

OTHER PUBLICATIONS

Balasubramanian, "Solvent dependent morphologies in thiol-ene photopolymerization: A facile route to the synthesis of resorcinarene nanocapsules", J. Mater. Chem., 2010, 20, 6539-6543.

Kalaitzis, "Solvent Dependent Morphologies in Thiol-Ene Photopolymerization: A Facile Route to Synthesis of Resorcinarene Nanocapsules", Master of Science in Chemistry, Old Dominion University, Dec. 2009.

Ramjee, "Resorcinarene Nanostructures: Synthesis and Functionalization", Department of Chemistry and Biochemistry, 41st National Organic Chemistry Symposium, University of Colorado, Jun. 7-11, 2009.

Tanaka, "Formation of Network and Cellular Structures by Viscoelastic Phase Separation," Adv. Mater. 2009, 21, 1872-1880.

S. E. A. Gratton, "The Pursuit of a Scalable Nanofabrication Platform for Use in Material and Life Science Applications," Acc. Chem. Res., 2008, 41, 1685-1695.

A. J. Meuler, "Ordered Network Mesostructures in Block Polymer Materials," Macromolecules, 2009, 42, 7221-7250.

L.E. Euliss, "Imparting size, shape, and composition control of materials for nanomedicine," Chem. Soc. Rev., 2006, 35, 1095-1104.

C.R. Martin, "Nanomaterials: A Membrane-Based Synthetic Approach," Science, 1994, 266, 1961-1966.

J. Lee, "Mesocellular polymer foams with unprecedented uniform large mesopores and high surface areas," Chem. Commun., 2004, 562-563.

S. Y. AN, "Preparation of monodisperse and size-controlled poly(ethylene glycol) hydrogel nanoparticles using liposome templates," Colloid Interface Sci., 2009, 331, 98-103.

J. P. Rolland, "Direct fabrication and harvesting of monodisperse, shape-specific nanobiomaterials," J. Am. Chem. Soc., 2005, 127, 10096-10100.

C. J. Hawker, "The convergence of synthetic organic and polymer chemistries," Science, 2005, 309, 1200-1205.

W. Meier, "Polymer nanocapsules," Chem. Soc. Rev., 2000, 29, 295-303.

F. Caruso, "Hollow capsule processing through colloidal templating and self-assembly," Chem.-Eur. J., 2000, 6, 413-419.

D. M. Vriezema, "Self-Assembled Nanoreactors," Chem. Rev., 2005, 105, 1445-1489.

R. K. O'Reilly, "Cross-linked block copolymer micelles: functional nanostructures of great potential and versatility," Chem. Soc. Rev., 2006, 35, 1068-1083.

E. S. Read, "Recent advances in shell cross-linked micelles," Chem. Commun., 2007, 3021-3035.

D. Lensen, "Polymeric Microcapsules for Synthetic Applications," Macromol. Biosci., 2008, 8, 991-1005.

X. W. Lou, "Hollow Micro-/Nanostructures: Synthesis and Applications," Adv. Mater., 2008, 3987-4019.

L. Sun, "Preparation of polycyclodextrin hollow spheres by templating gold nanoparticles," Chem. Commun., 2001, 359-360.

M. L. Wu, "Synthesis of nanometer-sized hollow polymer capsules from alkanethiol-coated gold nanoparticles," Chem. Commun., 2000, 775-776.

X. Liu, "Core functionalization of hollow polymer nanocapsules," J. Am. Chem. Soc., 2009, 131, 5718-5719.

A. D. Ievins, "Synthesis of hollow responsive functional nanocages using a metal-ligand complexation strategy," Macromolecules, 2008, 41, 3571-3578.

M. S. Wendland, "Synthesis of Cored Dendrimers," J. Am. Chem. Soc., 1999, 121, 1389-1390.

W. W.Li, "Reactive surfactants for polymeric nanocapsules via interfacially confined miniemulsion ATRP," Macromolecules, 2009, 42, 8228-8233.

C. E. Hoyle, "Thiol-Enes: Chemistry of the Past with Promise for the Future," J. Polym. Sci. Pol. Chem., 2004, 42, 5301-5338.

A. Dondoni, "The emergence of thiol-ene coupling as a click process for materials and bioorganic chemistry," Angew. Chem.-Int. Edit., 2008, 47, 8995-8997.

D. Kim, "Direct synthesis of polymer nanocapsules with a noncovalently tailorable surface," Angew. Chem.-Int. Edit., 2007, 46, 3471-3474.

K. M. Park, "Curcurbituril-based nanoparticles: a new efficient vehicle for targeted intracellular delivery of hydrophobic drugs," Chem. Commun., 2009, 71-73.

P. Timmerman, "Resorcinarenes," Tetrahedron, 1996, 52, 2663-2704.

R. Balasubramanian, "Encapsulation and functionalization of nanoparticles in crosslinked resorcinarene shells," J. Mater. Chem., 2007, 17, 105-112.

E. Roman, "Improved Synthesis of Cavitands," J. Org. Chem., 1999, 64, 2577-2578.

L. Pirondini, "Synthesis and Coordination Chemistry of Lower Rim Cavitand Ligands," Eur. J. Org. Chem., 2001, 2311-2320.

P. Crews, "Organic Structure Analysis," Oxford University Press, New York, 1998, 332.

M. Montalti, "Handbook of Photochemistry," 3rd edition, Taylor and Francis, Boca Raton, 2006, 541.

G. M. Burnett, "B. Chain Transfer and Inhibition. The Determination of Transfer Co-Efficients in Polymerisation Reactions," Discuss. Faraday Soc., 1947, 2, 322-328.

S. K. Das, "Studies in Chain Transfer. V. Acrylonitrile," Proc. R. Soc. London, Ser. A, 1955, 227, 252-258.

H. M. J. Boots, "Polymerization-Induced Phase Separation. 1. Conversion-Phase Diagrams," Macromolecules, 1996, 29, 7683-7689.

C. Serbutoviez, "Polymerization-Induced Phase Separation. 2. Morphology of POlymer-Dispersed Liquid Crystal Thin Films," Macromolecules, 1996, 29, 7690-7698.

J. W. Doane, "Field controlled light scattering from nematic microdroplets," Appl. Phys. Lett., 1986, 48, 269-271.

H. T. A. Wilderbeek, "Photo-initiated polymerization of liquid crystalline thiol-ene monomers in isotropic and anisotropic solvents," J. Phys. Chem. B, 2002, 106, 12874-12883.

K. Kimura, "Morphology Control of Poly(p-phenylene pyromelliteimide) by Means of Self-Assembling Polymerization," Macromolecules, 2003, 36, 6292-6294.

H. Tanaka,"Viscoelastic phase separation," J. Phys. Condens. Matter, 2000, 12, R207-R264.

A. J. Guenthner, "Morphology development in photopolymerization-induced phase separated mixtures of UV-curable thiol-ene adhesive and low molecular weight solvents," Polymer, 2008, 49, 5533-5540.

T. Inoue, "Reaction-induced phase decomposition in polymer blends," Prog. Polym. Sci., 1995, 20, 119-153.

G. Li, "Morphology evolution of polysulfone nanofibrous membranes toughened epoxy resin during reaction-induced phase separation," Mater. Chem. Phys., 2009, 118, 398-404.

D. F. O'Brien, "Polymerization of Preformed Self-Organized Assemblies," Acc. Chem. Res., 1998, 31, 861-868.

H. Tanaka, "Formation of Network and Cellular Structures by Viscoelastic Phase Separation," Adv. Mater., 2009, 21, 1872-1880.

International Search Report for PCT/US12/61307 dated Dec. 28, 2012.

E.S. Barrett, "Assembly and Exchange of Resorcinarene Capsules Monitored by Fluorescence Resonance Energy Transfer," J. Am. Chem. Soc., 2007, 129, 3818-3819.

Balasubramanian, "Solvent dependent morphologies in thiol-ene photopolymerization: A facile route to the synthesis of resorcinarene nanocapsules", J. Mater. Chem., 2010, 20, 6539-6543 (Supplementary Material included).

* cited by examiner

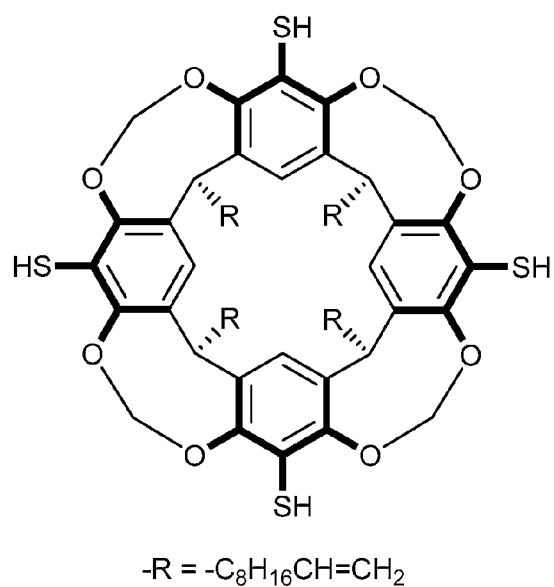
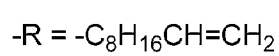
Fig. 1 Resorcinarene tetraalkene tetrathiol (RTATT)

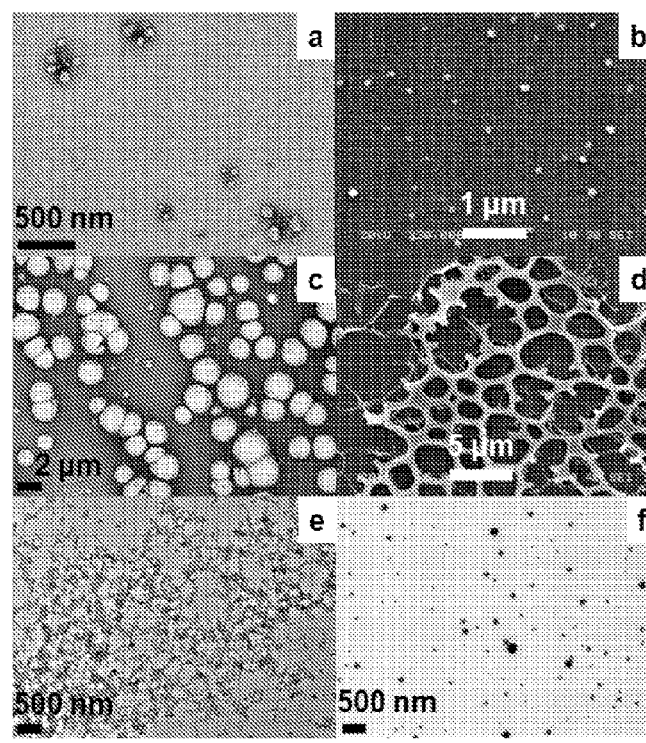
Fig. 2 Microscopic analysis of RTATT polymers prepared by UV irradiation for 3 h in various solvents.

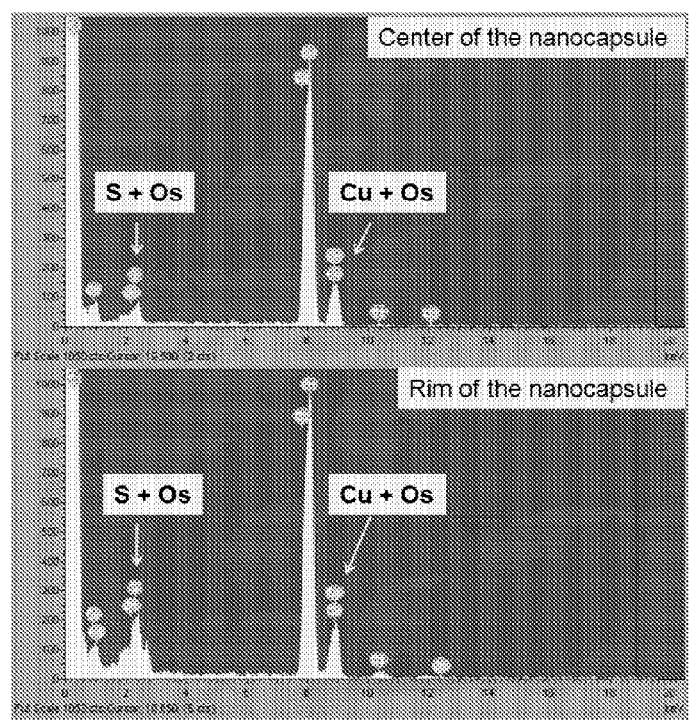
Fig. 3 EDS analysis of center (top) and rim (bottom) of the nanocapsules.

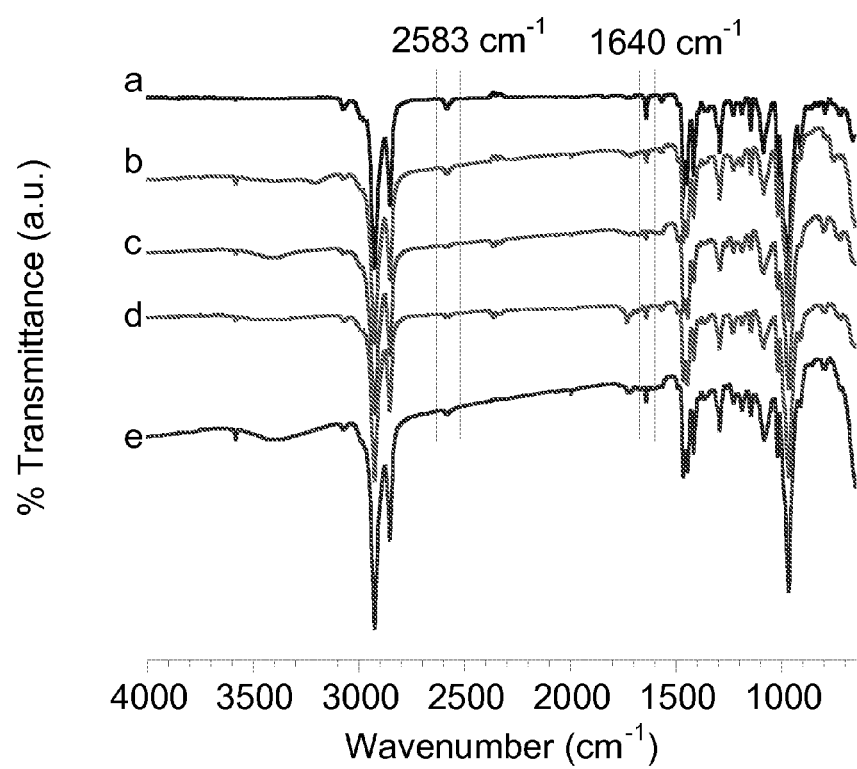
Fig. 4 IR spectra of RTATT monomer (a) and polymers (b)-(e)

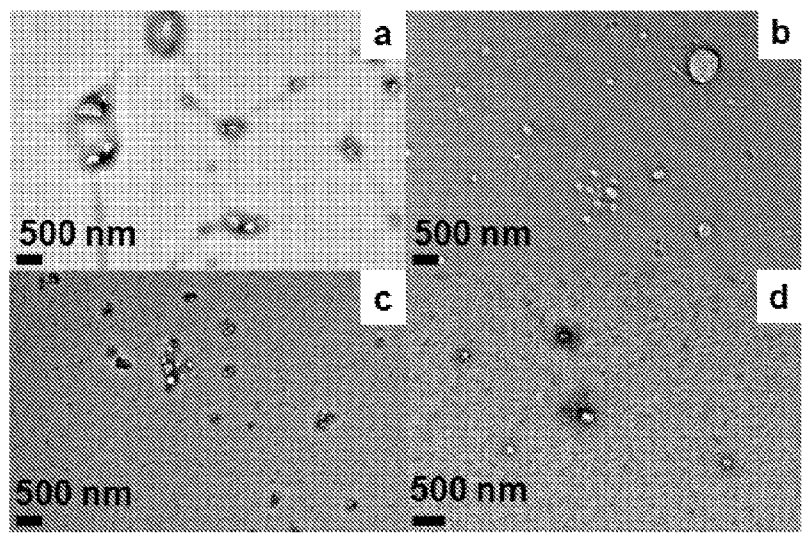
Fig. 5 TEM images of RTATT nanocapsules prepared in chloroform under various polymerization conditions.

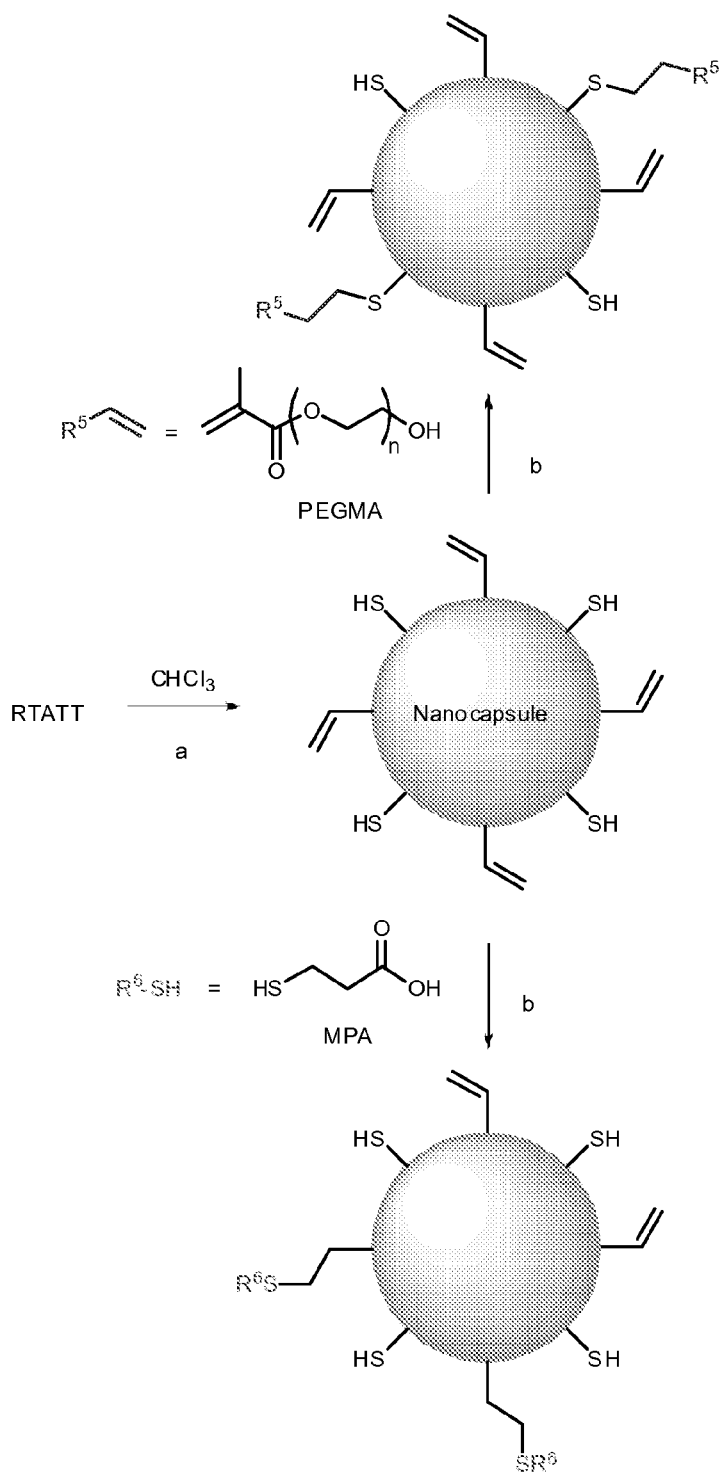
Fig. 6 - Example of one pot synthesis and functionalization of nanocapsules

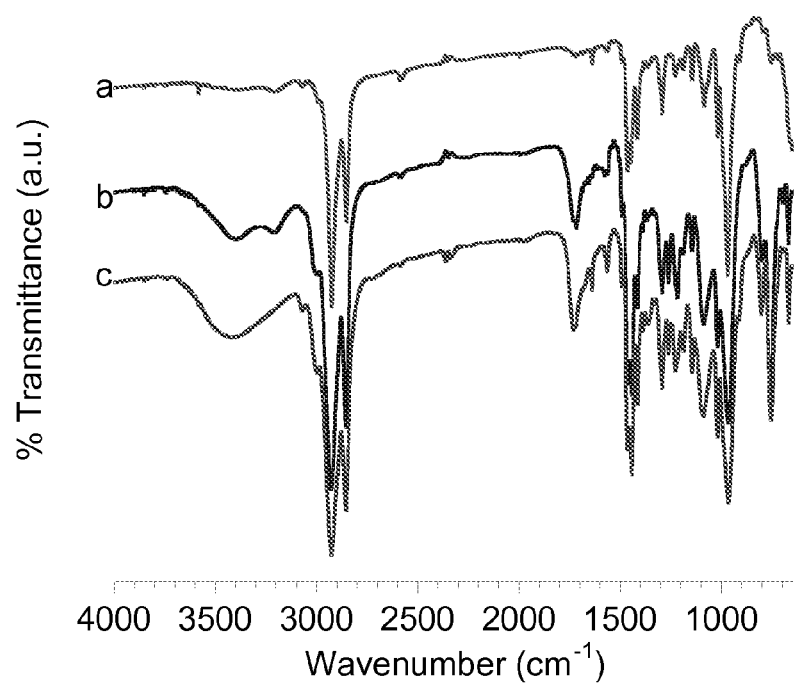
Fig. 7 - IR spectra of nanocapsules

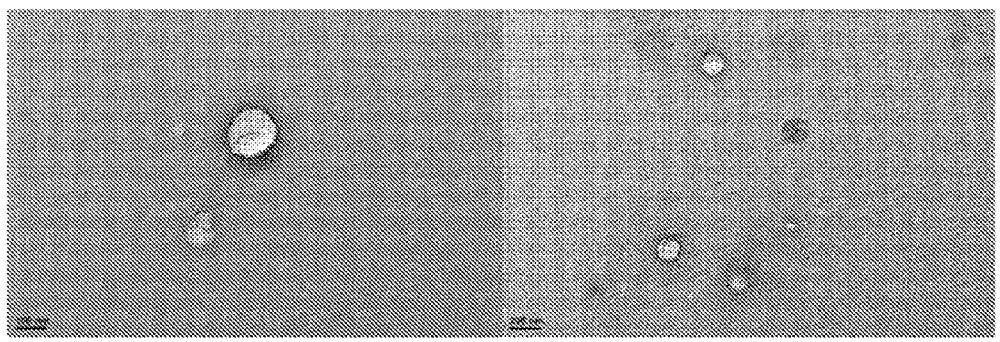
Fig. 8 – TEM images

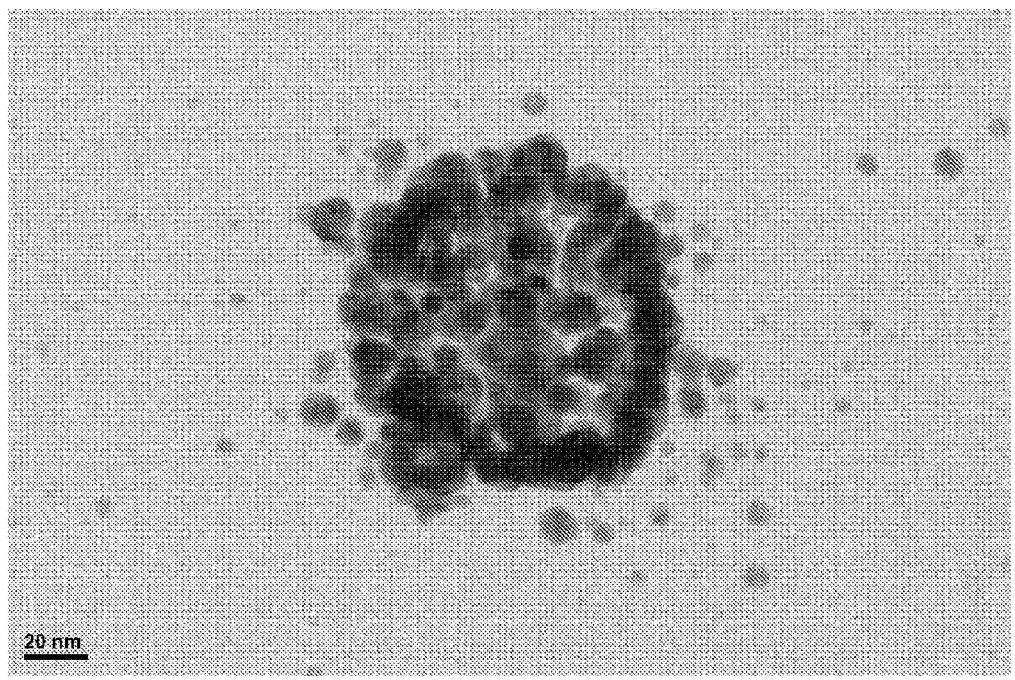
Fig. 9 – TEM image of RTATT nanocapsule – Au nanoparticle nanocomposite

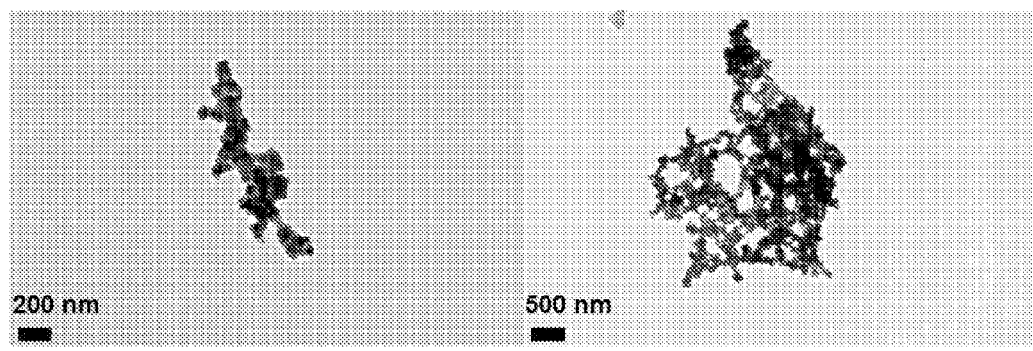
Fig. 10  Unstained TEM images of RTATT fibers (left) and fibrous network (right) structure templated gold nanoparticles.

FACILE ROUTE TO THE SYNTHESIS OF RESORCINARENE NANOCAPSULES

IN THE CROSS-REFERENCE TO RELATED APPLICATIONS

This application claims priority upon U.S. provisional application No. 61/356,707, filed Jun. 21, 2010, which is hereby incorporated herein by reference in its entirety for all purposes.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a direct method for the fabrication of resorcinarene nanocapsules by photopolymerization of compounds of formula (I), such as resorcinarene tetralkene tetrathiol (RTATT), in the absence of any template or preorganization. Further, by varying the polymerization media, a variety of other polymeric architectures like lattices, fibrous networks, and nanoparticles were obtained. The morphology and structure were characterized by transmission electron microscopy, energy dispersive spectroscopy, scanning electron microscopy, dynamic light scattering, infrared and nuclear magnetic resonance spectroscopy. These morphologically distinct resorcinarene polymeric architectures contain residual thiol and ene functional groups offering potential functionalization opportunities.

BACKGROUND OF THE INVENTION

The fabrication of precisely engineered polymeric nanostructures with control over their morphology and composition is vital for wide ranging applications from nanomedicine to material science (1). Synthesis of polymeric nanostructures is often achieved by self-assembly (2) or emulsion based "bottom-up" strategies, with limited control over size and shape (3). A wide range of templates like anodic aluminum oxide (4), mesocellular silica foam (5), liposomes (6), perfluoropolyether molds (7) etc. have been used for the synthesis of morphologically distinct polymers with varying degrees of success. In spite of the recent advances in organic synthesis and polymerization methods (8), there exists a strong need to develop new, simpler and direct routes to polymeric nanostructures with well-defined size, morphology and surface composition.

Among various polymeric architectures, hollow nanocapsules in particular have attracted enormous attention in recent years as drug delivery vehicles, nanoreactors, and in catalysis (9). While numerous approaches are available for the fabrication of nanocapsules and related nanocontainers (10) functionalization strategies are still in their infancy (10i)(10j). A variety of self-assembled nanocapsules mimicking biological systems (9)(10e) such as liposomes, polymersomes, and layer-by-layer capsules (10a) have been investigated. When compared to the non-covalently assembled structures, covalently linked polymeric nanocapsules offer crucial mechanical stability mandatory for a variety of applications (9). In the more popular template based approach a polymeric shell is grown around the template by a variety of means, following which the sacrificial template is selectively removed, resulting in the formation of nanocapsules (10). A number of templates including gold (10g) and silica nanoparticles (10a)(10f) self-assembled amphiphilic block copolymers (10a)(10c) and dendrimers (10k) have been employed for the synthesis of nanocapsules.

Over the years several surfactant stabilized emulsions have also been used for the synthesis of nanocapsules (10e). The techniques currently employed for the fabrication of nanocapsules require one of the following: self-assembly, sacrificial templates or emulsifiers (10e). These strategies have certain intrinsic limitations such as tedious procedures for the removal of sacrificial template or surfactants, lack of nanocapsule robustness, low efficiency etc. (10f)(10l).

Recently, Kim and coworkers have reported a direct synthesis of nanocapsules by employing thiol-ene photopolymerization of allyloxy cucurbituril with dithiol linkers (12). Resorcinarenes (13) are a well-established building block in supramolecular chemistry, with a rigid head and flexible tails, and are easily modified at either end. We envisaged that multiple thiol and ene functionalities could be introduced in a resorcinarene molecule, and most importantly these functionalities could be selectively placed in distinct locations, i.e., in the macrocyclic head or alkyl tail groups with widely differing rigidity, potentially resulting in novel nanostructures upon polymerization. Wei and coworkers have recently reported the use of RTATT, as a crosslinkable surfactant around gold nanoparticles using olefin-metathesis (14).

Surprisingly, it has been discovered that template-free polymerization of resorcinarenes is possible and that these resorcinarenes can be used to form nanocapsules and other polymeric architectures like lattices, fibrous network structures, and nanoparticles. The synthesis of the resorcinarene polymers are achieved by thiol-ene photopolymerization (11), a versatile polymerization tool with widespread applications and several attractive features like initiator-free initiation, functional group tolerance, and oxygen inhibition resistance.

SUMMARY OF THE INVENTION

The present invention relates to novel polymers of resorcinarenes which are formed by the thiol-ene photopolymerization of a compound of formula (I):

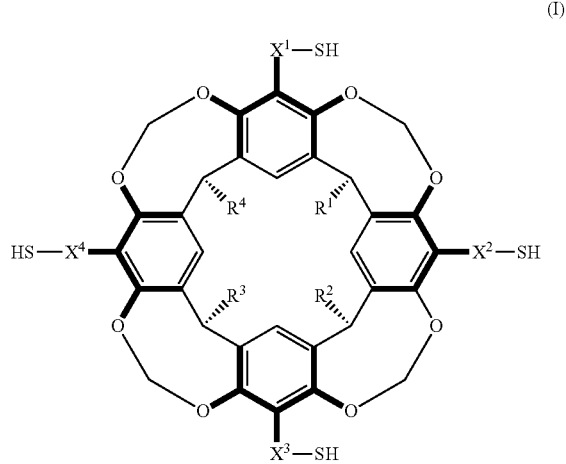

wherein:
$X^1$, $X^2$, $X^3$ and $X^4$ are independently —$(CH_2)_n$—;
n is from 0-8;
$R^1$, $R^2$, $R^3$ and $R^4$ are independently an alkene.

Another embodiment of the present invention is the process of making the polymer resorcinarenes of the invention by photopolymerization of the thiol and alkene moiety of the compound of formula (I).

Another embodiment of the present invention is a process of functionalizing the residual thiol or alkene moieties of the formed polymer of resorcinarene.

Another embodiment of the present invention is a process of stabilizing and encapsulating metal nanoparticles by adding nanocapsules formed by polymers of resorcinarenes.

The invention provides: (a) a direct, template-free fabrication of resorcinarene nanocapsules by thiol-ene photopolymerization; (b) generation of rich polymeric architectures by varying the photopolymerization reaction medium; (c) a one-pot synthesis and functionalization of resorcinarene nanocapsules; and (d) fabrication of hollow spherical metal nanoparticle assemblies with nanocapsule templates.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right and hereby disclose a disclaimer of any previously described product, method of making the product or process of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are apparent from and encompassed by, the following Detailed Description.

DETAILED DESCRIPTION OF THE INVENTION

The present invention relates to novel polymers of resorcinarenes which are formed by the thiol-ene photopolymerization of a compound of formula (I):

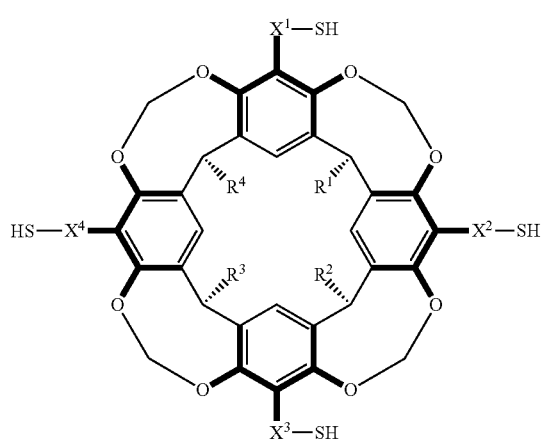

(I)

wherein:
$X^1$, $X^2$, $X^3$ and $X^4$ are independently —$(CH_2)_n$—;
n is from 0-8;
$R^1$, $R^2$, $R^3$ and $R^4$ are independently an alkene.

In one aspect of the resorcinarene polymer, for the compound of formula (I):
$X^1$, $X^2$, $X^3$ and $X^4$ are independently —$(CH_2)_n$—;
n is from 0-8;
$R^1$, $R^2$, $R^3$ and $R^4$ are independently a $C_2$-$C_{30}$ alkene.

In another aspect of the resorcinarene polymer, for the compound of formula (I):
n is 0;
$R^1$, $R^2$, $R^3$ and $R^4$ are independently a $C_{12}$-$C_{22}$ alkene.

In another aspect of the resorcinarene polymer, for the compound of formula (I):
n is 0;
$R^1$, $R^2$, $R^3$ and $R^4$ are independently a $C_4$-$C_{12}$ alkene.

In another aspect of the resorcinarene polymer, the alkene moiety is a terminal alkene.

In another aspect of the resorcinarene polymer, for the compound of formula (I):

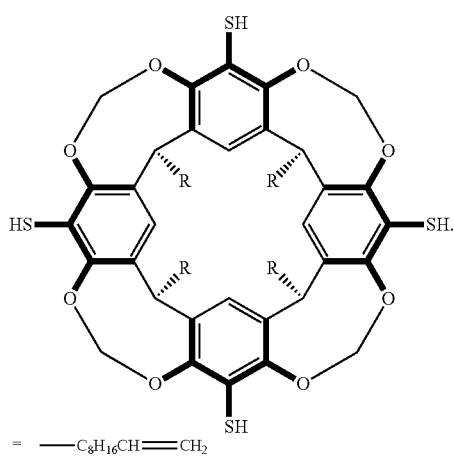

—R = —$C_8H_{16}CH$=$CH_2$

The present invention also relates to the formation of nanocapsules, lattices, fibrous networks and nanoparticles with the polymers of resorcinarenes which are formed by the thiol-ene photopolymerization of a compound of formula (I).

The present invention also relates to a process of making polymers of resorcinarenes via photopolymerization.

In another aspect of the process, the photopolymerization is between the thiol and alkene moieties of the compound of formula (I).

The present invention also relates to a process to functionalize the residual thiol or alkene moieties of the polymers of resorcinarenes with a functional group.

In another aspect of this process, the residual thiol is functionalized with either $R^5$—CH=$CH_2$ or $R^6$—SH, wherein:
$R^5$ and $R^6$ are independently —$C_1$-$C_4$-alkyl-OH, —$C_1$-$C_4$-alkyl-C(O)OH or —$C_1$-$C_4$-alkyl-C(O)O$R^7$,
wherein
$R^7$ is H, a —$C_1$-$C_4$-alkyl or —$(C_1$-$C_4$-alkyl-O$)_n$H wherein n is 0-4.

In another aspect of the process, the residual thiol is functionalized with a compound selected from the group consisting of poly(ethylene glycol) methacrylate (PEGMA), 3-mercaptopropionic acid (MPA), 3-butenoic acid and 3-mercaptopropanol.

The present invention also relates to a process of stabilizing and encapsulating metal nanoparticles by adding nanocapsules formed by polymers of resorcinarenes to the metal nanoparticles.

In another aspect of this process, the metal of the metal nanoparticles is selected from the group consisting of a metal from Groups 4-12 of the Periodic Table. (Groups 4-12 metals refers to the nomenclature recognized by the International Union of Pure and Applied Chemistry (IUPAC) as of 21 Jan. 2011; may also be recognized under CAS as being Group IVB-VIIB, VIII, IB and IIB). The metal nanoparticles may be obtained by methods known in the art, e.g. reduction of metal salts to form metal nanoparticles.

In another aspect of this process, the metal of the metal nanoparticles is selected from the group consisting of a metal Au, Ag, Cd, Hg, Os, Pb, Pt, Pd, Rh, Ru and Zn. In another aspect of the invention, the metal of the metal nanoparticles is, selected from the group consisting of Au, Ag, Pt, Pd, Rh, and Ru.

In another aspect of the process, the metal nanoparticles are gold (Au) nanoparticles.

The present invention also relates to compositions which comprise the metal nanoparticles stabilized and encapsulated in the polymers of resorcinarenes.

In another aspect of the composition, the compound stabilized and encapsulated by the polymers of resorcinarenes is a compound which can fit in the cavity of the polymers of resorcinarenes.

In another aspect of the composition the polymers of resorcinarene is in the form of a nanocapsule.

In another aspect of the composition, the cavity of the nanocapsule has a diameter is about 80-100 nm in diameter.

It is further noted that the direct, template-free synthesis and in situ functionalization method for nanopcapsules, substantially reduces the number of synthetic operations typically employed. Moreover, given the surface engineering via the inventive one-pot synthesis and functionalization approach and their inherent guest encapsulation capability, the nanocapsules and nanoparticle-nanocapsule composites of the invention are ideal platforms for "theranostic nanomedicine". (The integration of diagnostic and therapeutic functions is labeled as "theranostic nanomedicine".)

Distinct Morphological Development

It is well-known that the phase separation of monomers and oligomers during polymerization, referred to as polymerization induced phase separation (PIPS), can result in various morphologies depending upon the initial composition and reaction conditions (20). For example, PIPS has been widely employed in the fabrication of polymer-dispersed liquid crystal films (21). The increasing size of the growing polymer chain is often cited as the main reason for phase separation (20), though reaction solvent is also known to play a key role (22). In addition, for crosslinkable systems, the elasticity of the network formed must also be considered (20a). Recently, viscoelastic phase separation theory, which also factors in the slower dynamics of polymers in solution, has been used to explain a variety of unusual phase separation phenomena (23). Currently, there is an interest in modulating the relative influence of phase separation and viscoelastic effects by varying the polymerization solvent to generate a wide-range of morphologies (24).

Scheme 1 Schematic representation of RTATT photopolymerization.

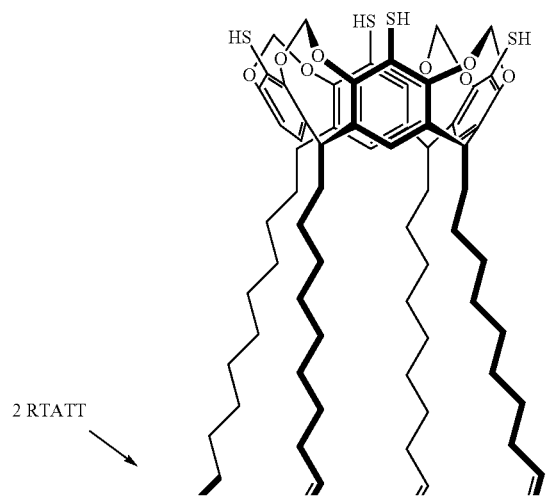

2 RTATT

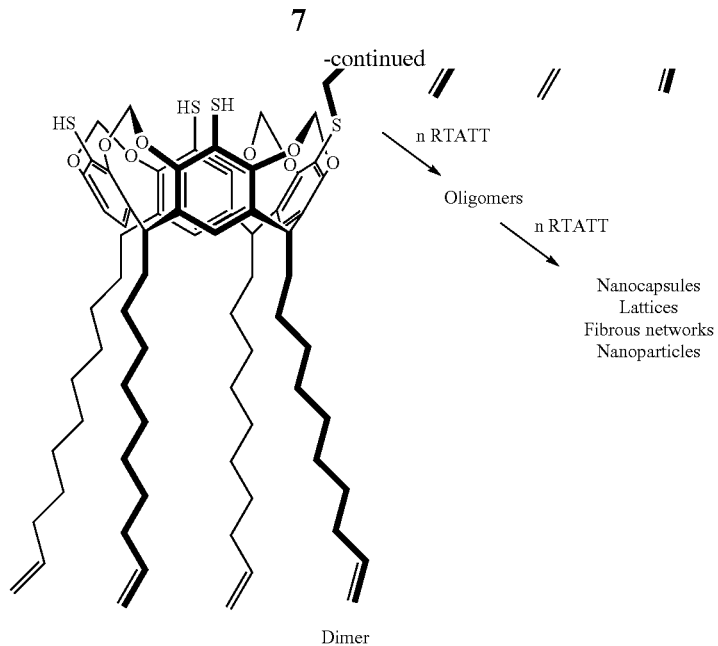

Dimer

On the basis of the available experimental evidence and the relevant literature (20)(23-25). we propose the following model for the development of morphologically distinct polymeric architectures in various solvents. Initially, a RTATT dimer (Scheme 1) is formed through a sulfide linkage. The dimer is expected to polymerize further into oligomeric species upon reaction with monomers (26), although the rate of oligomerization or polymerization may be solvent dependent. The formation of morphologically distinct polymeric structures in various solvents could be a function of two antagonistic effects (25), thiol-ene polymerization-rate or reaction extent and phase separation effects, as the rate of the crosslinking reaction is known to suppress the phase separation by slowing down the polymer diffusion. A closer look at the IR spectra (FIG. 4) revealed that the photoproducts synthesized in dichloromethane and ethyl acetate contained reduced amounts of residual thiol (2583 cm$^{-1}$) when compared to those prepared in either chloroform or tetrahydrofuran. The RTATT polymerization reactions with higher reaction progress (with dichloromethane and ethyl acetate as reaction media) led to fibrous or lattice networks in contrast to those with lower conversion (from chloroform and tetrahydrofuran) leading to the formation of spherical nanoparticles. Indeed, it is documented that the early onset of phase separation at lower conversion is known to result in formation of spherical particles, whereas the late onset of phase separation with high conversion produces web-like, sparse networks (20b)(24).

However, this does not explain the formation of hollow nanocapsules. Although the detailed mechanism for the formation of resorcinarene nanocapsules needs further investigation, it could be similar to the non-covalent assembly of lipids (27). Lipid assembly into various morphologically distinct architectures is fundamentally determined by opposing forces such as curvature energy and geometry dependent energy terms, which includes hydrocarbon packing energy, van der Waals attraction energy, electrostatic repulsion energy, and hydration repulsion energy (27). The lipid system adjusts to system changes by a change of morphology (27). In a similar vein, recently Kim and coworkers invoked the initial formation of a two dimensional disk like oligomeric intermediate, and its bending to reduce its total energy to explain the covalent synthesis of cucurbituril hollow nanocapsule by thiol-ene photopolymerization (12a).

Currently, detailed kinetic studies of RTATT photopolymerization and thermal characterization of resorcinarene polymers are in progress in our laboratories and the results will be reported in due course.

Factors Influencing the Formation of Nanocapsules

Among various resorcinarene polymeric architectures obtained by photopolymerization, the formation of resorcinarene nanocapsules in chloroform from RTATT monomer is remarkable in the absence of any template or preorganized structure. It is also worth noting that the photopolymerization of a two component system comprising resorcinarene cavitand and triethylene glycol-dithiol did not result in the formation of nanocapsules under identical conditions.

To obtain further insights into the RTATT nanocapsule formation, we varied both the initial monomer concentration (1.5 mM) and photopolymerization duration (3 h). Not surprisingly (22b) the initial monomer concentration plays a crucial role in the formation of nanocapsules. We noticed linear structures (FIG. 5a, further confirmed by SEM in addition to polydisperse nanocapsules at lower RTATT monomer concentration (0.75 mM), which were absent at higher monomer concentrations (FIGS. 2a, 2b and 5b). Most importantly, we observed that nanocapsules were formed even in the very early stages (15 min) of photopolymerization (FIG. 5c). We did not notice any significant changes in size or shape of nanocapsules formed (FIG. 5d) upon increasing the photopolymerization duration to 20 h. However, occasionally longer reaction times lead to some solvent evaporation, resulting in the formation of macroscopic sheets.

The invention is further described by the following non-limiting examples which further illustrate the invention, and are not intended, nor should they be interpreted to, limit the scope of the invention.

BRIEF DESCRIPTION OF THE DRAWINGS

FIG. 1 depicts the structure for resorcinarene tetraalkene tetrathiol (RTATT).

FIG. 2 depicts microscopic analysis of RTATT polymers prepared by UV irradiation for 3 h in various solvents: TEM (a) and SEM (b) of RTATT nanocapsules prepared in chloroform; TEM (c) and SEM (d) of RTATT nanocapsules prepared in dichloromethane; (e) nanocapsules prepared in ethyl acetate; and (f) nanocapsules prepared in tetrahydrofuran.

FIG. 3 depicts EDS analysis of center (top) and rim (bottom) of the nanocapsules.

FIG. 4 depicts IR spectra of RTATT monomer (a) and polymers obtained by photopolymerization for 3 h in chloroform (b), dichloromethane (c), ethyl acetate (d), and tetrahydrofuran (e).

FIG. 5 depicts TEM images of RTATT nanocapsules prepared in chloroform under various polymerization conditions. RTATT monomer concentration and reaction duration were a) 0.75 mM, 3 h. b) 3.0 mM, 3 h. c) 1.5 mM, 15 min. and d) 1.5 mM, 20 h. TEM (JEOL JEM-2100F, 200 kV) analysis was performed on osmium tetroxide stained samples.

FIG. 6 depicts and example of one pot synthesis and functionalization of nanocapsules: a) photopolymerization for 3 h and b) photopolymerization for 10 min. The circle is intended as shorthand for RTATT without the $R^1$, $R^2$, $R^3$ and $R^4$ groups.

FIG. 7 depicts IR spectra of nanocapsules a) before functionalization and dialyzed samples of b) MPA and c) PEGMA functionalized nanocapsules.

FIG. 8 depicts TEM images of MPA (left) and PEGMA (right) functionalized nanocapsules.

FIG. 9 depicts TEM image of RTATT nanocapsule—Au nanoparticle nanocomposite.

FIG. 10 depicts unstained TEM images of RTATT fibers (left image) and fibrous network (right image) structure templated gold nanoparticles.

EXAMPLES

Experimental

All solvents used in this study were dried and distilled by following standard procedures prior to their use. Synthesis of RTATT has been described in detail elsewhere (14). Synthesis of the resorcinarene cavitand was carried out from the corresponding resorcinarene, by following Kaifer's sealed tube method (15), and its spectral data was consistent with those reported in the literature (16). TEM and SEM images reported in this article are for as prepared samples, unless otherwise specified.

Example 1

Photopolymerization

RTATT (18.5 mg) dissolved in 10 mL of solvent was filtered through a 0.45 μm nylon membrane and transferred into a quartz tube. The reaction mixture was degassed with argon for 30 s and sealed prior to UV irradiation for 3 h. All photopolymerization experiments were carried out in closed quartz vessels at room temperature in a Srinivasan-Griffin Rayonet photochemical reactor, equipped with four 254 nm (~35 watts) and four 300 nm (~21 watts) lamps, supplied by the Southern New England Ultraviolet Company.

Characterization

TEM and EDS analysis were carried out in a JEOL JEM-2100F field emission microscope operating at 200 kV equipped with an Oxford INCAx-sight EDS detector and a Gatan SC1000 ORIUS CCD camera (11 megapixel). Samples for TEM analysis were stained by mixing the photopolymerized reaction mixture (18.5 mg/10 mL solvent) with an equal volume of 0.1% aqueous $OsO_4$ solution for at least 1 h with occasional shaking. The stained samples were deposited on a carbon coated copper grid.

SEM images were obtained using a JEOL JSM-6060LV scanning electron microscope operating at 5-30 kV. SEM samples were prepared by depositing dilute solutions of RTATT photopolymers (18.5 mg/10 mL solvent) on a freshly cleaned glass slide followed by deposition of a thin layer of gold to prevent charging.

Dynamic light scattering experiments were performed on a Zetasizer nano series model: ZEN 3200 (Malvern Instruments). IR analysis of solution dropcast polymer samples was carried out on a Thermo Electron Nicolet 370 DTGS spectrophotometer operating in transmission mode. Nanocapsules synthesized in chloroform (10 mL) were evaporated, dried under reduced pressure and redispersed in $CDCl_3$ (1 mL) prior to $^1$H-NMR analysis. $^1$H-NMR analysis of polymeric nanocapsules was carried out on a Varian Oxford 400 MHz instrument with a d1 of 10 s. Size exclusion chromatography of nanocapsules was carried out in a Shimadzu HPLC system equipped with a JAIGEL 2.5H column, PDA and differential refractive index detectors, and chloroform (3.5 mL/min) as eluent.

Example 2

In Situ Surface Functionalization of Nanocapsules

Nanocapsules with residual thiol and ene groups offered exciting possibilities for surface functionalization under photopolymerization reaction conditions by further reaction with other thiol or ene groups. A general representation of the simple one-pot two-stage photopolymerization reaction for the synthesis and surface functionalization of nanocapsules is illustrated in FIG. 6 (28). Experiments were performed by functionalizing with representative thiol and ene compounds like 3-mercaptopropionic acid (MPA) and poly(ethylene glycol) methacrylate (PEGMA, MW ~360).

In a typical surface functionalization experiment, RTATT solution in chloroform (1.5 mM) was irradiated for 3 h to generate nanocapsules, to which MPA or PEGMA (1 equiv) was added and UV irradiation continued for an additional 10 min. Unreacted MPA or PEGMA was removed by either dialysis or an aqueous workup. IR spectra (FIG. 7) of functionalized nanocapsules clearly showed the presence of carboxyl (1700 cm$^{-1}$) and hydroxyl groups (3400 cm$^{-1}$), confirming the incorporation of MPA or PEGMA on the nanocapsules (17). Detailed structural characterization of such functionalized nanocapsules is currently underway in our laboratories.

Example 3

Nanocapsules with thiol and sulfide linkages were envisaged as effective templates for stabilizing and encapsulating metal nanoparticles (Scheme 2). Proof-of-the concept experiment was carried out by reducing gold salt ($HAuCl_4$) in the presence of RTATT nanocapsules.

Scheme 2 General scheme for templating metal nanoparticles

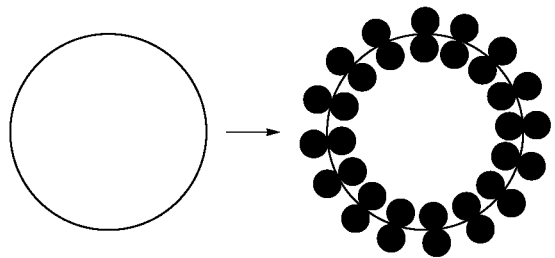

In a typical experiment, tetraoctylammonium bromide (0.1 g; 0.18 mmol) in CHCl$_3$ (10 mL) was added to a solution of HAuCl$_4$ (20.6 mg, 0.06 mmol) dissolved in H$_2$O (5 mL) and vigorously stirred. After 10 minutes, metal salt from the aqueous phase was completely transferred into the organic layer as evidenced by the color changes in aqueous and organic phases: the aqueous layer became colorless from pale yellow solution and the organic layer became orange-brown from colorless. The organic phase was separated and the nanocapsules prepared in chloroform (~9 mL) were added and stirring continued for an additional 30 minutes. The metal salt-nanocapsule mixture was cooled to 0° C., and an ice cold aqueous solution of sodium borohydride (31 mg, 0.82 mmol; 2 mL of H$_2$O) was added and stirred at 0° C. for 1 h. The nanoparticle-nanocapsule composites in organic phase were collected and washed with copious amounts of water. Their analysis was carried out by Transmission electron microscopy (FIG. 9).

FIG. 9 clearly shows a gold shell of ~115 nm with individual gold nanoparticles (~10 nm) uniformly distributed all over the nanoshells. Note that the periphery of the shell (FIG. 9) is much darker implying multilayer gold packing when compared to the inner core with a few layers of gold nanoparticles stacked on each other. A control experiment with RTATT monomer as stabilizer did not generate such nanoshells. These experiments clearly demonstrate the metal nanoparticle templating capabilities of the nanocapsules employed.

In principle, the templating strategy of Example 3 can be applied to other resorcinarene nanostructures. HAuCl$_4$ was reduced with sodium borohydride, in the presence of RTATT fibrous networks prepared by photopolymerization in ethyl acetate. As shown in FIG. 10 both gold nanoparticle network structures (left image) and short individual gold nanoparticle fibers (left image) were obtained; demonstrating the capability of both fibers and network structures to act as templating agents for gold nanoparticle assembly. The individual gold nanoparticles in the fibers/fibrous networks were slightly larger and somewhat partially elongated when compared to those formed in the nanocapsules.

Results and Discussion
Polymerization and Morphological Characterization

In a typical photopolymerization experiment, a degassed RTATT solution (1.5 mM in dried and freshly distilled solvent) was irradiated for 3 h in a Rayonet reactor equipped with both 254 nm and 300 nm lamps (see experimental section for further details). We chose chloroform, dichloromethane, ethyl acetate, and tetrahydrofuran as reaction media due to the excellent solubility of RTATT monomer in these solvents. In our experiments with chloroform, dichloromethane, ethyl acetate and tetrahydrofuran as reaction media, there was no visible (macro)phase separation after 3 h of photopolymerization. RTATT polymers synthesized in various solvents exhibited substantial differences in morphology (FIG. 2), as characterized by transmission electron microscopy (TEM) and scanning electron microscopy (SEM). A variety of distinct morphological architectures like nanocapsules, fibrous network structures, nanoparticles, and network lattices were observed (FIG. 2).

Remarkably, polymerization in chloroform resulted in the formation of nanocapsules. The hollow nature of the nanocapsule could be confirmed by TEM analysis (FIG. 2a), which showed the formation of a darker rim with a lighter core. Further, energy dispersive spectroscopy (EDS) analysis conducted on the rim and center of a nanocapsule under identical conditions showed enhanced S content on the rim, when compared to the center of the nanocapsule, as indicated by a higher $I_{(S+Os)}/I_{(Cu+Os)}$ ratio for the spectrum taken from the rim (FIG. 3), suggesting a hollow nature. Note that the intensity for the Os peaks were taken into account, due to their overlapping with the Cu and S peaks, with Cu originating from the grid and Os from the staining agent. SEM analysis (FIG. 2b) of nanocapsules gave an average size of 106±18 nm which was in good agreement with the particle size analysis from dynamic light scattering data (DLS). In addition to nanocapsules (~100 nm), some RTATT oligomers (<10 nm) were also observed in DLS. Further, size exclusion chromatographic (SEC) analysis provided additional evidence for the formation of such oligomeric species.

With dichloromethane as the polymerization media, both TEM and SEM (FIGS. 2c and 2d) showed the presence of network lattice structures that extended several microns, with both nano and micrometer sized pores. EDS analysis of these network structures showed comparable S content in between and on the lattices, perhaps suggesting a multilayer network architecture. Polymerization in ethyl acetate led to a fibrous structure (FIG. 2e) where, in addition to ribbon like fibers of various dimensions (top left and lower right of FIG. 2e), porous network structures were also observed. Even after dilution, both individual fibers and network structures were observed, ruling out drying effects. Polymerization of RTATT in tetrahydrofuran (FIG. 2f) yielded almost spherical polydisperse (85±53 nm) nanoparticles that were uniformly dark.

Overall, the observed morphological features were quite reproducible and on a practical note no noticeable changes were observed even upon substitution of dried and distilled solvents with commercially available reagent grade solvents. Such dramatic differences in morphological features upon photopolymerization in various solvents required additional probing, given the identical reaction conditions such as initial concentration, temperature, duration and lack of significant evaporation.

To establish that the thiol-ene photopolymerization indeed took place (11a) i.e., the reaction between alkene and thiol groups resulted in the formation of sulfide linkages, the photopolymers were investigated by infrared (IR) and nuclear magnetic resonance (NMR) spectroscopy. The IR spectra of polymers obtained by photopolymerization of RTATT in various solvents (FIG. 4), though similar to RTATT monomer showed reduced peak intensities at both 2583 cm$^{-1}$ (SH) and 1640 cm$^{-1}$ (C=C) as expected (17). The evidence for the formation of sulfide linkage was provided by $^1$H-NMR spectroscopy. In agreement with the IR data, the $^1$H-NMR spectra of RTATT subjected to UV irradiation in chloroform showed reduced intensities at the multiplets centered around 5.8 and 4.95 ppm (terminal alkene groups) and the singlet at 3.79 ppm (thiol groups). In addition, the broad peak at ~2.6 ppm in the NMR could be attributed to the —CH$_2$—S— linkages formed by thiol-ene photopolymerization.

Careful examination of the IR spectra (FIG. 4) revealed that the extent of reduction of 2583 cm$^{-1}$ (SH) and 1640 cm$^{-1}$ (C═C) peaks was different for polymers obtained from different solvents, suggesting differential polymerization progress, perhaps reflecting differential polymerization rates of RTATT in various solvents. This result is not entirely surprising given the variable 254 nm UV radiation transmission efficiency of the solvents examined (18) and the well-established chain transfer characteristics of chloroform (19).

We have demonstrated a simple, template-free, thiol-ene photopolymerization reaction for the fabrication of resorcinarene nanocapsules. The formation of nanocapsules was susceptible to changes in concentration and polymerization media. In addition to nanocapsules, the polymerization experiments can be tuned to yield lattices, fibrous networks, or nanoparticles, by varying the solvent. We have shown that nanocapsules are formed even in the very early stages of polymerization.

REFERENCES (1) S. E. A. Gratton, S. S. Williams, M. E. Napier, P. D. Pohlhaus, Z. L. Zhou, K. B. Wiles, B. W. Maynor, C. Shen, T. Olafsen, E. T. Samulski and J. M. Desimone, *Acc. Chem. Res.*, 2008, 41, 1685-1695.

(2) A. J. Meuler, M. A. Hillmyer and F. S. Bates, *Macromolecules*, 2009, 42, 7221-7250.

(3) L. E. Euliss, J. A. DuPont, S. Gratton and J. DeSimone, *Chem. Soc. Rev.*, 2006, 35, 1095-1104.

(4) C. R. Martin, *Science*, 1994, 266, 1961-1966.

(5) J. Lee, J. Kim, S. W. Kim, C. H. Shin and T. Hyeon, *Chem. Commun.*, 2004, 562-563.

(6) S. Y. An, M. P. N. Bui, Y. J. Nam, K. N. Han, C. A. Li, J. Choo, E. K. Lee, S. Katoh, Y. Kumada and G. H. Seong, *J. Colloid Interface Sci.*, 2009, 331, 98-103.

(7) J. P. Rolland, B. W. Maynor, L. E. Euliss, A. E. Exner, G. M. Denison and J. M. DeSimone, *J. Am. Chem. Soc.*, 2005, 127, 10096-10100.

(8) C. J. Hawker and K. L. Wooley, *Science*, 2005, 309, 1200-1205.

(9) W. Meier, *Chem. Soc. Rev.*, 2000, 29, 295-303.

(10) (a) F. Caruso, *Chem.-Eur. J.*, 2000, 6, 413-419.
(b) D. M. Vriezema, M. C. Aragones, J. Elemans, J. Cornelissen, A. E. Rowan and R. J. M. Nolte, *Chem. Rev.*, 2005, 105, 1445-1489.
(c) R. K. O'Reilly, C. J. Hawker and K. L. Wooley, *Chem. Soc. Rev.*, 2006, 35, 1068-1083.
(d) E. S. Read and S. P. Armes, *Chem. Commun.*, 2007, 3021-3035.
(e) D. Lensen, D. M. Vriezema and J. C. M. van Hest, *Macromol. Biosci.*, 2008, 8, 991-1005.
(f) X. W. Lou, L. A. Archer and Z. C. Yang, *Adv. Mater.*, 2008, 20, 3987-4019.
(g) L. Sun, R. M. Crooks and V. Chechik, *Chem. Commun.*, 2001, 359-360.
(h) M. L. Wu, S. A. O'Neill, L. C. Brousseau, W. P. McConnell, D. A. Shultz, R. J. Linderman and D. L. Feldheim, *Chem. Commun.*, 2000, 775-776.
(i) X. Liu and A. Basu, *J. Am. Chem. Soc.*, 2009, 131, 5718-5719.
(j) A. D. Ievins, A. O. Moughton and R. K. O'Reilly, *Macromolecules*, 2008, 41, 3571-3578.
(k) M. S. Wendland and S. C. Zimmerman, *J. Am. Chem. Soc.*, 1999, 121, 1389-1390.
(l) W. W. Li, K. Matyjaszewski, K. Albrecht and M. Moller, *Macromolecules*, 2009, 42, 8228-8233.

(11) (a) C. E. Hoyle, T. Y. Lee and T. Roper, *J. Polym. Sci. Pol. Chem.*, 2004, 42, 5301-5338.
(b) A. Dondoni, *Angew. Chem.-Int. Edit.*, 2008, 47, 8995-8997.

(12) (a) D. Kim, E. Kim, J. Kim, K. M. Park, K. Baek, M. Jung, Y. H. Ko, W. Sung, H. S. Kim, J. H. Suh, C. G. Park, O, S, Na, D. K. Lee, K. E. Lee, S. S. Han and K. Kim, *Angew. Chem.-Int. Edit.*, 2007, 46, 3471-3474.
(b) K. M. Park, K. Suh, H. Jung, D. W. Lee, Y. Ahn, J. Kim, K. Baek and K. Kim, *Chem. Commun.*, 2009, 71-73.

(13) P. Timmerman, W. Verboom and D. N. Reinhoudt, *Tetrahedron*, 1996, 52, 2663-2704.

(14) R. Balasubramanian, Y. G. Kwon and A. Wei, *J. Mater. Chem.*, 2007, 17, 105-112.

(15) E. Roman, C. Peinador, S. Mendoza and A. E. Kaifer, *J. Org. Chem.*, 1999, 64, 2577-2578.

(16) L. Pirondini, D. Bonifazi, E. Menozzi, E. Wegelius, K. Rissanen, C. Massera and E. Dalcanale, *Eur. J. Org. Chem.*, 2001, 2311-2320.

(17) P. Crews, J. Rodriguez, M. Jaspars, *Organic Structure Analysis*, Oxford University Press, New York, 1998, 332.

(18) M. Montalti, A. Credi, L. Prodi, M. T. Gandolfi, *Handbook of Photochemistry, $3^{rd}$ edition*, Taylor and Francis, Boca Raton, 2006, 541.

(19) (a) G. M. Burnett and H. W. Melville, *Discuss. Faraday Soc.*, 1947, 2, 322-328.
(b) S. K. Das, S. R. Chatterjee and S. R. Palit, *Proc. R. Soc. London, Ser. A*, 1955, 227, 252-258.

(20) (a) H. M. J. Boots, J. G. Kloosterboer, C. Serbutoviez and F. J. Touwslager, *Macromolecules*, 1996, 29, 7683-7689.
(b) C. Serbutoviez, J. G. Kloosterboer, H. M. J. Boots and F. J. Touwslager, *Macromolecules*, 1996, 29, 7690-7698.

(21) J. W. Doane, N. A. Vaz, B. G. Wu and S. Zumer, *Appl. Phys. Lett.*, 1986, 48, 269-271.

(22) (a) H. T. A. Wilderbeek, M. G. M. van der Meer, C. W. M. Bastiaansen and D. J. Broer, *J. Phys. Chem. B*, 2002, 106, 12874-12883.
(b) K. Kimura, J. H. Zhuang, K. Wakabayashi and Y. Yamashita, *Macromolecules*, 2003, 36, 6292-6294.

(23) (a) H. Tanaka, *J. Phys. Condens. Matter*, 2000, 12, R207-R264. (b) H. Tanaka, *Adv. Mater.*, 2009, 21, 1872-1880.

(24) A. J. Guenthner, D. M. Hess and J. J. Cash, *Polymer*, 2008, 49, 5533-5540.

(25) (a) T. Inoue, *Prog. Polym. Sci.*, 1995, 20, 119-153.
(b) G. Li, Z. B. Huang, C. L. Xin, P. Li, X. L. Jia, B. H. Wang, Y. D. He, S. Ryu and X. P. Yang, *Mater. Chem. Phys.*, 2009, 118, 398-404.

(26) It must be noted that under these reaction conditions (ref 12a) the formation of side products like disulfide linkages may also be formed.

(27) D. F. O'Brien, B. Armitage, A. Benedicto, D. E. Bennett, H. G. Lamparski, Y. S. Lee, W. Srisiri and T. M. Sisson, *Acc. Chem. Res.*, 1998, 31, 861-868.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:
1. A composition comprising metal nanocapsules encapsulated in a resorcinarene polymer, wherein the resorcinarene polymer is formed by the thiol-ene photopolymerization of a compound of formula (I):

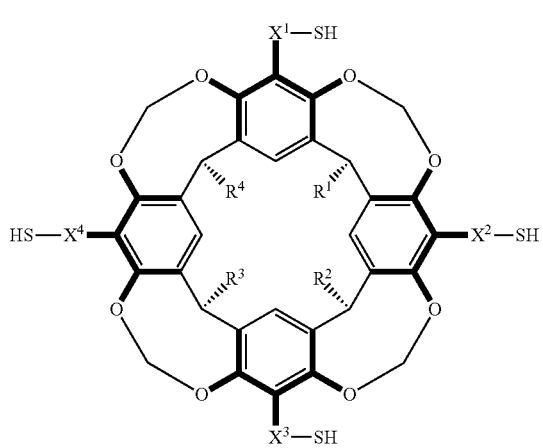

(I)

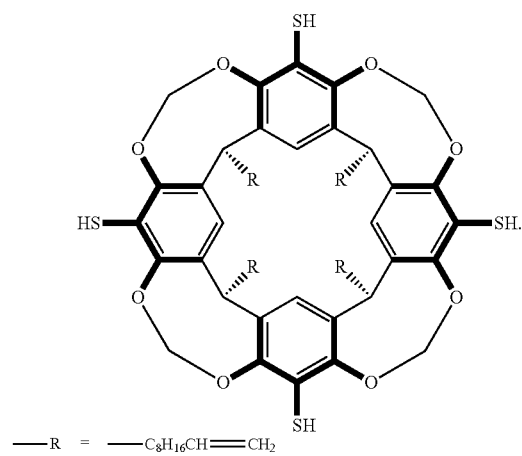

—R = —C$_8$H$_{16}$CH═CH$_2$ wherein:
$X^1$, $X^2$, $X^3$ and $X^4$ are independently —(CH$_2$)$_n$—;
n is from 0-8; and
$R^1$, $R^2$, $R^3$ and $R^4$ are independently an alkene.

2. The compositon of claim 1, wherein for the compound of formula (I):
$X^1$, $X^2$, $X^3$ and $X^4$ are independently —(CH$_2$)$_n$—;
n is from 0-8;
$R^1$, $R^2$, $R^3$ and $R^4$ are independently a C$_2$-C$_{30}$ alkene.

3. The compositon of claim 2, wherein for the compound of formula (I):
n is 0;
$R^1$, $R^2$, $R^3$ and $R^4$ are independently a C$_{12}$-C$_{22}$ alkene.

4. The compositon of claim 3, wherein for the compound of formula (I):
n is 0;
$R^1$, $R^2$, $R^3$ and $R^4$ are independently a C$_4$-C$_{12}$ alkene.

5. The compositon of claim 1, wherein the compound of formula (I) is:

6. The compositon of claim 1, wherein the resorcinarene polymer is formed by the thiol-ene photopolymerization of a compound of formula (I) in chloroform, dichloromethane, ethyl acetate, or tetrahydrofuran.

7. The compositon of claim 1, wherein the resorcinarene polymer is formed by the thiol-ene photopolymerization of a compound of formula (I) in chloroform.

8. The compositon of claim 1, wherein the metal nanoparticles are selected from the group consisting of a metal from Groups 4-12 of the Periodic Table.

9. The compositon of claim 1, wherein the metal nanoparticles are selected from the group consisting of a metal Au, Ag, Cd, Hg, Os, Pb, Pt, Pd, Rh, Ru and Zn.

10. The compositon of claim 1, wherein the metal nanoparticles are gold nanoparticles.

* * * * *